(12) United States Patent
Kriz et al.

(10) Patent No.: US 10,132,820 B2
(45) Date of Patent: Nov. 20, 2018

(54) DISPOSABLE ANALYTICAL MICROPROCESSOR DEVICE

(75) Inventors: Dario Kriz, Lund (SE); Kirstin Ann Kriz, Lund (SE)

(73) Assignee: Lifeassays AB, Lund (SE)

(*) Notice: Subject to any disclaimer, the term of this patent is extended or adjusted under 35 U.S.C. 154(b) by 1971 days.

(21) Appl. No.: 12/201,898

(22) Filed: Aug. 29, 2008

(65) Prior Publication Data

US 2009/0061418 A1 Mar. 5, 2009

Related U.S. Application Data

(60) Provisional application No. 60/967,291, filed on Sep. 1, 2007.

(51) Int. Cl.
*G01N 35/00* (2006.01)
*A61B 5/145* (2006.01)
*G01N 33/487* (2006.01)

(52) U.S. Cl.
CPC ... *G01N 35/00732* (2013.01); *A61B 5/14546* (2013.01); *G01N 33/48792* (2013.01); *A61B 5/14532* (2013.01); *A61B 2562/0295* (2013.01); *G01N 2035/00683* (2013.01); *G01N 2035/00811* (2013.01); *G01N 2035/00851* (2013.01); *Y10T 436/144444* (2015.01)

(58) Field of Classification Search
CPC ... G01N 35/00732; G01N 2035/00683; G01N 2035/00811; G01N 2035/00851; G01N 33/48792; A61B 5/14532; A61B 5/14546; A61B 2562/0295
USPC ........... 702/19–23, 30–32; 422/502; 700/266
See application file for complete search history.

(56) References Cited

U.S. PATENT DOCUMENTS

| | | | |
|---|---|---|---|
| 4,799,635 A | 1/1989 | Nakagawa | |
| 4,975,647 A | 12/1990 | Downer et al. | |
| 5,053,199 A | 10/1991 | Keisler et al. | |
| 5,366,609 A | 11/1994 | White et al. | |
| 6,295,506 B1 * | 9/2001 | Heinonen et al. | 702/104 |
| 6,392,894 B1 | 5/2002 | Buechler et al. | |
| 6,579,690 B1 * | 6/2003 | Bonnecaze et al. | 435/14 |
| 6,602,469 B1 | 8/2003 | Maus et al. | |

(Continued)

FOREIGN PATENT DOCUMENTS

| | | |
|---|---|---|
| EP | 1 147 739 A | 10/2001 |
| EP | 1 729 128 A | 12/2006 |
| WO | WO 2004/051971 | 1/1989 |

OTHER PUBLICATIONS

Notification of Transmittal of the International Search Report and the Written Opinion of the International Searching Authority, or the Declaration for International Application No. PCT/US2008/074844 dated Apr. 12, 2008, 14 pages.

(Continued)

*Primary Examiner* — Shogo Sasaki
(74) *Attorney, Agent, or Firm* — Hahn Loeser & Parks, LLP (57) ABSTRACT

The present invention generally relates to the determination of an analyte concentration (quantitative determination) or whether an analyte threshold level has been passed (qualitative determination) in a biological sample through employment of a disposable analytical microprocessor device. The device can include a batch-specific, self-executable algorithm for the calculation of the analyte concentration.

20 Claims, 4 Drawing Sheets

(56) References Cited

U.S. PATENT DOCUMENTS

| | | |
|---|---|---|
| 2002/0170823 A1 | 11/2002 | Housefield |
| 2003/0038047 A1* | 2/2003 | Sleva et al. .................. 206/370 |
| 2004/0209371 A1 | 10/2004 | Conlon et al. |
| 2005/0113650 A1* | 5/2005 | Pacione et al. .............. 600/300 |
| 2006/0178914 A1* | 8/2006 | Brown ............................. 705/3 |
| 2006/0222568 A1* | 10/2006 | Wang et al. ................... 422/70 |
| 2006/0248554 A1* | 11/2006 | Priddy ........................... 725/25 |

OTHER PUBLICATIONS

Office Action, mailed in related Chinese Patent Application No. 200880109894.0, dated Sep. 24, 2012.

Office Action, mailed in related Chinese Patent Application No. 200880109894.0, dated Jun. 21, 2013.

\* cited by examiner

DISPOSABLE ANALYTICAL MICROPROCESSOR DEVICE

RELATED APPLICATION

This application claims priority to U.S. Provisional Patent Application Ser. No. 60/967,291 filed Sep. 1, 2007; which is incorporated by reference herein in its entirety.

BACKGROUND

The quantitative and qualitative determination of an analyte in a biological sample can be done using a variety of physical and chemical analytical devices. These devices typically include, for example, a receptacle, port, or the like, for receiving test media; equipment for sensing test results (a sensing meter); and an algorithm used for analysis of test results. The quantitative and/or qualitative determination of most analytes requires the presence of a recognition element, which recognizes and interacts with the analyte. After the initial recognition step (which in some cases can include, for example, a chemical reaction, a biological reaction, or the like), this reaction event is translated by a sensing meter into a physically measurable signal. The signal can thereafter be correlated to the amount of analyte in the biological sample through the use of the algorithm.

A disposable consumable, when exposed to a certain analyte concentration, outputs a concentration-dependent signal indicative of manifestations of a chemical or physical reaction in the disposable consumable. Thus, a large number of disposable consumables must be manufactured and delivered to various places in the world. The reproducibility of each individual batch of disposable consumables affects the quantitative and qualitative determinations. In many situations, including, for example, point-of-care applications involving analyte detection, a sufficient performance must be guaranteed. This can be accomplished by employing calibration data that are specific for each manufactured batch of the disposable consumables. Such calibration data have been, according to references, manually or automatically inserted into the analytical device where the analytical device uses a pre-determined, non-adjustable algorithm, and/or, a pre-determined adjustable algorithm, which can partially be upgraded with new batch specific computer code.

BACKGROUND ART

U.S. Pat. No. 5,366,609 to White et al., describes a blood glucose and cholesterol meter for use with disposable sample strips, with an insertable pluggable memory key containing a plurality of stored parameter values and procedure routines. The insertable pluggable memory key does not provide a new, batch-specific, self-executable algorithm.

U.S. Pat. No. 5,053,199 to Keiser et al., describes a biosensing meter for sample strips employing sensing or reflectance techniques for detection of analytes in blood samples. A removable memory-based chip enables batch-specific parameters to be automatically loaded from the Read Only Memory (ROM) to the meter. The removable memory does not contain any algorithms.

U.S. Pat. No. 4,975,647 to Downer et al., describes an analytical machine such as a chromatography system with a pluggable memory module that employs consumable fluid reagents. The module contains parameters such as timing of calibration operations, fluid container information, and concentration of fluids. The information is used to handle calibration and operation of the machine. In one example of the analytical machine, the pluggable memory module contains variables such as a conventional two-byte cyclic redundancy check (CRC) word for error management. The removable memory does not contain any self-executable algorithms.

The references above fail to address problems such as low sensing meter adaptability to changes such as, for example, new analytes, improved protocols, and the like, safe transfer of data between the sensing meter and pluggable memories, and protection from unauthorized access to the batch-specific parameters values and other information transferred to the sensing meter from the pluggable memories, or low protection level to lock the sensing meter operation if unauthorized pluggable memories are used.

SUMMARY

Among the various embodiments of the invention is the provision of a disposable analytical microprocessor device capable of reversible engagement with a sensing meter, with the disposable analytical microprocessor device capable of bidirectional transfer of data with the sensing meter. Embodiments of the device also include stored batch-specific parameter values of disposable consumables, a microprocessor; and at least one self-executable algorithm able to calculate an analyte concentration value using data received from the sensing meter in combination with said stored batch-specific data. The device can then transfer the value to the sensing meter.

In some embodiments, the device includes a one-chip microcomputer which contains a microprocessor. In some embodiments, the reversible engagement capability enables serial and or parallel, or a combination thereof, bidirectional transfer of said data. In some embodiments, the reversible engagement capability provides electrical connectivity and further provides the microprocessor with a clock pulse from an oscillator in the sensing meter.

In some embodiments of the invention the reversible engagement capability can include an optical connection, and enables bidirectional transfer of data. In some embodiments the self-executable algorithm is based on a reference table conversion, or on a mathematical function approximation wherein the function is a linear function, or a polynomial function. In some embodiments, the self-executable algorithm is based on a logarithmic function, or an exponential function, or a trigonometric function In some embodiments, stored batch-specific parameter values or the self-executable algorithm are stored in an internal memory of a one-chip microcomputer or in a separate RAM, ROM, EPROM, EEPROM based memory chip in the device.

In some embodiments of the invention the stored batch-specific parameter values contain information about specific analyte calculation performance of a batch of disposable consumables, for example mathematical approximation formulas, encryption keys, analyte name in ASCI-code, the production batch number, the batch production date, the batch expiration date, number of measurements allowed, analyte identification data, the dates when each individual disposable consumable was used, the remaining number of disposable consumables in the end-user package, the individual identification number of said sensing meter used, the individual identification of the person operating the sensing meter, measuring and/or timing protocols, high-low alarm level analyte concentration values, or any combination thereof.

In some embodiments of the invention the stored parameter values can include an encrypted key for secure data transfer between said microprocessor and the sensing meter. Some embodiments can include a battery powered electronic date chip with a real-time clock, and a calendar which provides internal time and date information to said self-executable algorithm.

In some embodiments of the invention, the self-executable algorithm execution can be disabled by changing from its active operating state to its non-active state operation state when the stored parameter values or the data show that a predetermined number of used disposable consumables has been exceeded, or that the expiration date of the batch has been exceeded, or that the individual identification number of the sensing meter used has been changed, or that the an encrypted key does not correspond to the encrypted key in the sensing meter, or that a measuring procedure error has been reported from the sensing meter.

Some embodiments of the invention provide a system for determining the concentration of an analyte in a sample, such system including the disposable analytical microprocessor device and a sensing meter.

In some embodiments of the invention, the sensing meter can include means for measuring magnetic permeability changes in the disposable consumables when exposed to said analyte, and, for outputting signals to the microprocessor indicative of manifestations of a chemical or physical reaction in disposable reagent vials or strips.

In some embodiments, the sensing meter further includes equipment for measuring optical changes including, for example, absorbance, polarization, fluorescence, electrochemi-luminescence, turbidity, nephelometric, or refractometric, in disposable reagent vials or disposable reagent strips, when exposed to an analyte, and, for outputting signals to the microprocessor indicative of manifestations of a chemical or physical reaction in the disposable consumables.

In some embodiments of the invention, the sensing meter can include means for measuring electrochemical changes such as amperometry, polarometry or conductometry in the disposable reagent vials or disposable reagent strips when exposed to said analyte, and, for outputting signals to a microprocessor indicative of manifestations of a chemical or physical reaction in the disposable consumables.

In some embodiments of the invention, the sensing meter can include means for measuring mass changes in the disposable reagent vials or disposable reagent strips when exposed to an analyte, and, for outputting signals to a microprocessor indicative of manifestations of a chemical or physical reaction in said disposable consumables. In some embodiments of the disclosed subject matter, the sensing meter can also include means for measuring piezoelectric changes or surface plasmon effects in disposable reagent vials or disposable reagent strips when exposed to an analyte, and, for outputting signals to a microprocessor indicative of manifestations of a chemical or physical reaction in the disposable consumables.

In some embodiments of the disclosed subject matter, the sensing meter can include means for measuring any of the analytes glucose, albumin, hemoglobin (Hb and HbA1C), myoglobin, troponin (I and T), CK-MB, creatinine kinase (CK), d-dimer, very low density lipoprotein (VLDL), β-type natriuretic peptide (BNP and pro BNP), n-terminal prohormone peptide (NT-proBNP), C-reactive protein (hsCRP and CRP), cystatin C, prothrombin, activated partial thromboplastin (APTT), HCG, LH, FSH, PSA, TSH, T3, T4, AFP, CEA, low density lipoprotein (LDL), high density lipoprotein (HDL), triglycerides, cholesterol, antibodies, *Streptococcus A, Helicobacter Pylori, Salmonella, Chlamydia, Giardia*, cholera, hepatitis (A, B and C), adenovirus, rotavirus, and the like, or any combination thereof with disposable consumables when exposed to an analyte, and for outputting signals to the processor chip indicative of manifestations of a chemical or physical reaction in the disposable consumables.

In some embodiments of the disclosed subject matter, the sensing meter can include an electronic date chip containing a real-time clock and a calendar which provides time and date information to the said self-executable algorithm.

Various embodiments of the disclosed subject matter provide a method for determining an analyte concentration in a biological sample, such methods including applying a biological sample to a disposable consumable, and introducing a disposable consumable to the device.

Other objects and features will be in part apparent and in part pointed out hereinafter.

BRIEF DESCRIPTION OF THE DRAWINGS

Those of skill in the art will understand that the drawings, described below, are for illustrative purposes only. The drawings are not intended to limit the scope of the present teachings in any way.

DETAILED DESCRIPTION

Analytical devices within the field of the invention are exemplified by, for example, spectrophotometers, polarimeters, fluorescence meters, light reflectance meters, light scattering meters, light absorbance meters, biosensors, chromatography system, amperometric devices, conductometric devices, magnetic permeability meters, and the like.

Concentration values for a plurality of analytes have been determined using various analytical devices. In the medical field, examples of analytes include, for example: glucose, albumin, hemoglobin (Hb and HbA1C), myoglobin, troponin (I and T), CK-MB, creatinine kinase (CK), d-dimer, very low density lipoprotein (VLDL), β-type natriuretic peptide (BNP and pro BNP), n-terminal prohormone peptide (NT-proBNP), C-reactive protein (hsCRP and CRP), cystatin C, prothrombin, activated partial thromboplastin (APTT), HCG, LH, FSH, PSA, TSH, T3, T4, AFP, CEA, low density lipoprotein (LDL), high density lipoprotein (HDL), triglycerides, cholesterol, antibodies, *Streptococcus A, Helicobacter Pylori, Salmonella, Chlamydia, Giardia*, cholera, hepatitis (A, B and C), adenovirus, rotavirus, and the like.

The recognition element is exemplified but not limited to, for example, a peptide, a protein, an enzyme, an antibody, a dry-chemistry reagent, organic, inorganic molecules, and the like.

The molecular recognition between the recognition element and the analyte can be based on many different types of interactions, such as, for example, electrostatic, hydrophobic, hydrogen bonds, Van der Waals, electrochemical changes, mass changes, optical changes (for example, absorbance, polarization, fluorescence, electrochemi-luminescence, turbidity, and the like), piezoelectric changes, surface plasmon effects, temperature, changes of the magnetic permeability, and the like.

Analytical devices based on the use of disposable consumables are used in many locations such as, for example, hospitals, hospital wards or departments, emergency rooms, ambulances, primary care, primary care health centers, community health centers, doctors' or physicians' offices, rehabilitation centers, elderly care facilities, other point-of-care locations, private homes, field-use locations, companies, industrial laboratories, universities, governmental institutes and agencies, and the like. Analytical devices can be used for various purposes such as, for example, clinical chemistry applications, point-of-care diagnostics and treatment applications, patient testing, employee testing, athletic testing, self-testing, mass screening, veterinary applications, agriculture applications, environmental survey applications, automated analytical robots for laboratories applications, medical device applications, military applications, regulatory applications, quality control applications, and the like.

Embodiments of the invention provide to a sensing meter a high degree of adaptability, as the meter can use for each batch a completely new external self-executable algorithm. The algorithm can contain, for example, stored batch-specific parameter values, mathematical approximation formulas, encryption keys, an analyte name in ASCI-code, batch expiration dates, a limit on the number of measurements allowed, analyte-identification data, measuring and/or timing protocols, high and/or low analyte concentration limits, and the like. Further, embodiments of the invention can provide completely new protocols for analyzing new analytes without the need for redesign, replacement and/or reprogramming of the sensing meter.

An additional advantage of embodiments of the invention is that the self-executable algorithm of the disposable analytical microprocessor device offers a very high degree of security against unauthorized access as it performs an internal calculation of the analyte concentration. None of the stored batch-specific parameter values are sent to the sensing meter, and thus they are not susceptible to unauthorized access. Furthermore, the disclosed device can internally activate itself and operate for a pre-determined period or pre-determined number of tests, after which the sensing meter will not have access to new analyte calculations and is effectively locked from operation.

An additional advantage of embodiments of the invention is providing a sensing meter with a disposable analytical microprocessor device containing an encryption key which ensures better quality control, better security control, and better regulatory control over the results obtained, as well as lower risk for unauthorized reversed engineering. This is especially significant when embodiments of the invention are used with sensing meters for medical applications, such as hospital laboratory testing and point-of-care testing.

An additional advantage of the disclosed subject matter is that the sensing meter can be made more flexible and adaptable to completely new analytes, as it can use the stored analyte name in ASCI-code in some embodiments of the invention to present the correct analyte name on the sensing instrument display. Thus, completely new analyte identifications can be added to a sensing meter located at the end-user without the need to upgrade the sensing meter.

An additional advantage of the disclosed subject matter is that the sensing meter can be less complex and less expensive, as it does not require its own algorithm, which reduces the number of electrical components in the sensing meter.

Accordingly, it is an object of embodiments of the invention to provide a sensing meter with a disposable analytical microprocessor device containing a batch specific self-executable algorithm for the calculation of the analyte concentration.

Embodiments of the invention include a disposable analytical microprocessor device containing at least one batch-specific self-executable algorithm for the qualitative or quantitative determination of analytes in a biological sample, employing disposable consumables. Embodiments of the invention can attach to a sensing meter, and enables the sensing meter to use an external self-executable algorithm which can contain stored batch-specific parameter values such as mathematical approximation formulas. Furthermore, additional parameters such as, for example, encryption keys, the production batch number, the batch production date, the batch expiration date, number of measurements allowed, analyte identification data, and the like, can also be included. Date of use for each individual disposable consumable, the remaining number of disposable consumables in the end-user package, the individual identification number of said sensing meter used, the individual identification of the person operating said sensing meter, measuring/timing protocols, high-low alarm level analyte concentration values, and the like, can all be included, without the need for redesign, replacement and/or reprogramming of the sensing meter itself. The delivery of a new algorithm with each batch of the disposable consumables introduces flexibility to continuously improve the performance of the quantitative and qualitative determinations.

Figure 1:
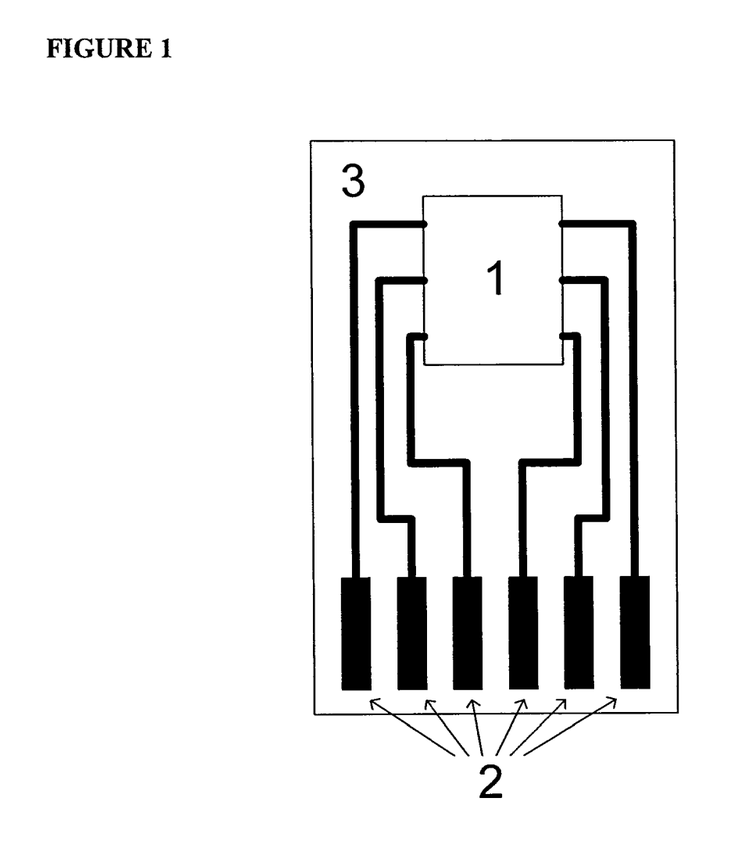
FIG. 1. A plan view of the disposable analytical microprocessor device containing an electrical interface for bidirectional data transfer.

Referring now to FIG. 1, in some embodiments of the disclosed subject matter the disposable analytical microprocessor device includes a one-chip microcomputer 1 which contains a batch specific self-executable algorithm for the calculation of the analyte concentration, external sensing meter electrical connectors 2 for power supply feeding of the one-chip microcomputer 1 and for electrical bidirectional communication enabling serial or parallel data transfer between the one-chip microcomputer 1 and the attached external sensing meter. The one-chip microcomputer 1 and the external sensing meter electrical connectors 2 are attached to a standard printed circuit board (PCB) 3.

Figure 2:
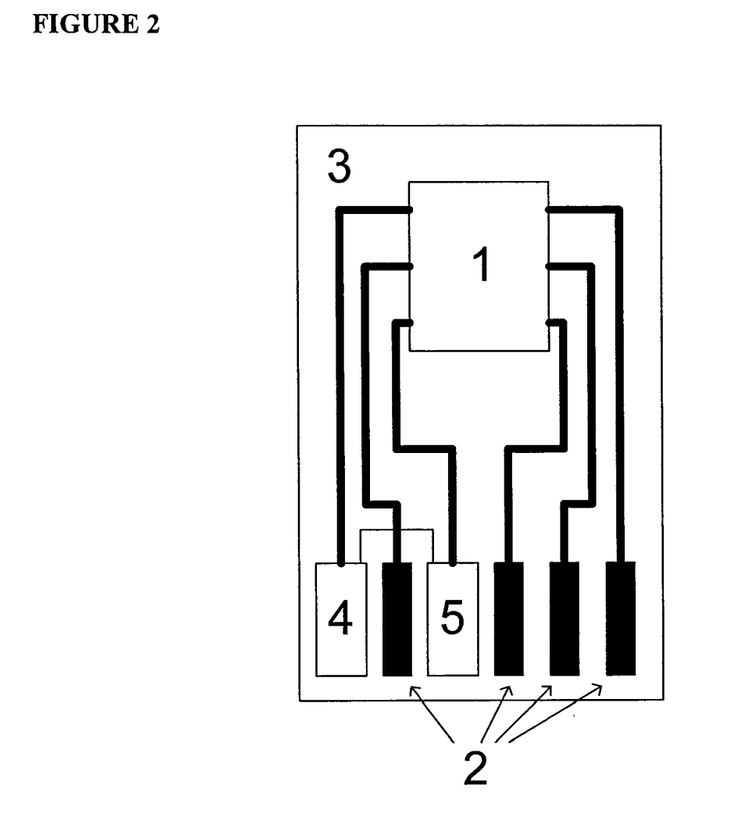
FIG. 2. A plan view of the disposable analytical microprocessor device containing an optical interface for bidirectional data transfer.

Referring now to FIG. 2, in some embodiments of the disclosed subject matter the disposable analytical microprocessor device includes a one-chip microcomputer 1 which contains a batch specific self-executable algorithm for the calculation of the analyte concentration, external sensing meter electrical connectors 2 for power supply feeding of the one-chip microcomputer 1, data sending optical transmitter 4 exemplified by a standard light-emitting diode (laser, visual light, UV or IR) for optical unidirectional communication enabling serial data transfer from the one-chip microcomputer 1 to the attached external sensing meter, data receiving optical device 5 exemplified by a standard photo transistor for optical unidirectional communication enabling serial data transfer to the one-chip microcomputer 1 from the attached external sensing meter. The one-chip microcomputer 1, the external sensing meter electrical connectors 2, data sending optical transmitter 4, and the data receiving optical device 5 are attached to a standard printed circuit board (PCB) 3.

Figure 3:
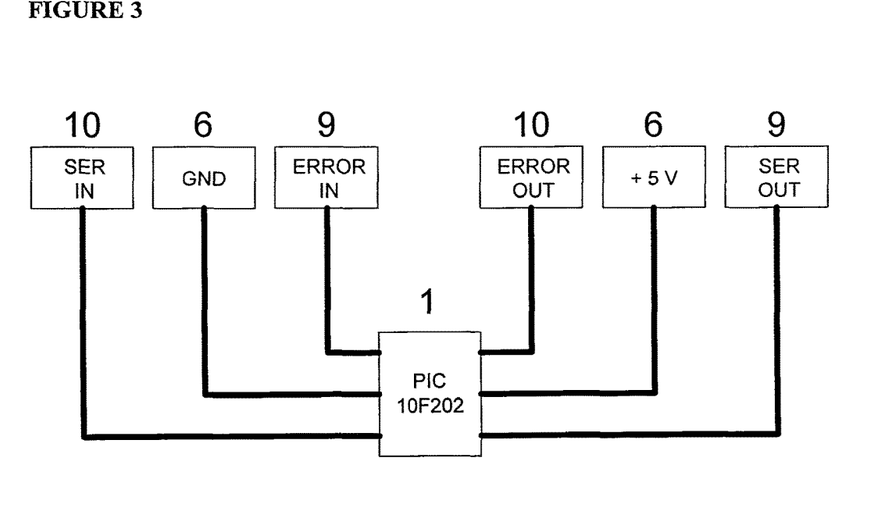
FIG. 3. A circuit diagram of a one-chip microcomputer containing batch-specific self-executable algorithm for the calculation of the analyte concentration and equipped with sensing instrument data transfer connections.

Referring now to FIG. 3, a schematic is shown of circuitry within some embodiments of the disclosed subject matter of the disposable analytical microprocessor device, and illustrates a one-chip microcomputer 1 exemplified by the PIC10F202 (from Microchip), a +5 Volt power supply 6, a ground connection (GND) 7, output pin for sending serial data 9, input pin for receiving serial data 8, output error pin 10 for sending error message to the sensing meter, and an input error pin 11 for receiving error message from the sensing meter.

Figure 4:
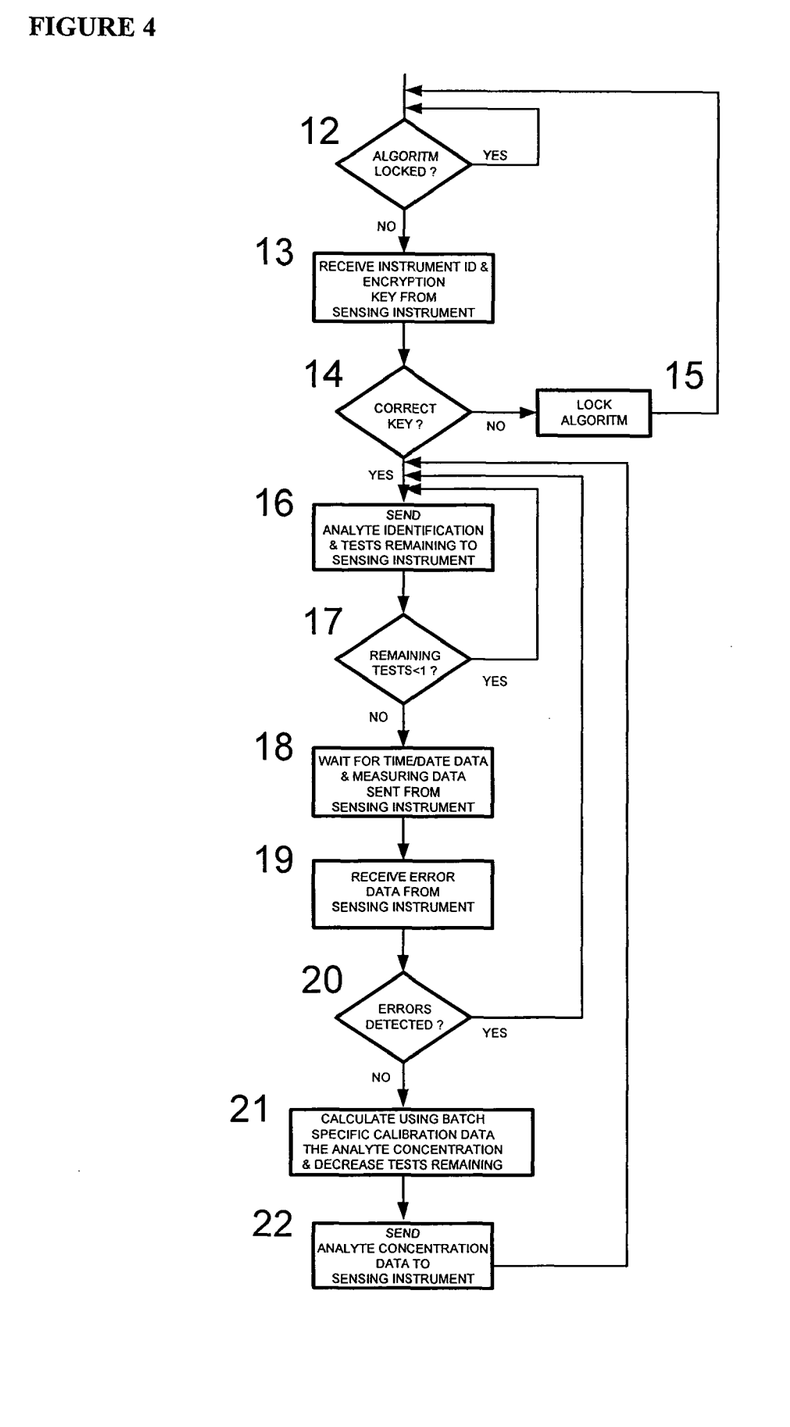
FIG. 4. A high level flow diagram which illustrates an algorithm for safe data transfer and a batch-specific quality controlled analyte concentration value calculation.

A batch specific self-executable algorithm programmed in the one-chip microcomputer 1 is shown in FIG. 4. The algorithm starts automatically when the disposable analytical microprocessor device is connected into the sensing meter and thereby it is provided the +5 Volt power supply 6 and the ground connection 7. After this power-on start, the algorithm checks 12 if it has been permanently locked during previous execution. If the algorithm has been permanently locked it will not be able to continue executing processes 13-22. If the algorithm has not been permanently locked it will proceed and load 13 the instrument identification (ID) and the encryption key sent from the sensing instrument. If no key is sent, the algorithm will continue waiting for a key. If an encryption key has been received, the algorithm proceeds to verify the key 14 by controlling if the received encryption key corresponds to a pre-stored encryption key in the one-chip microcomputer 1. If the wrong encryption key is sent, the algorithm will permanently lock 15 and return to start.

If the correct encryption key is sent, the algorithm will proceed to send 16 an analyte identification number and information about how many remaining tests that the disposable analytical microprocessor device will allow the end-user to perform to the sensing meter. Thereafter, the algorithm checks if the number of remaining tests is less than one. If the number of remaining tests is less than one, the algorithm will return to execute process 16 and the sensing instrument will continue inform the end-user that zero tests remain. If the number of remaining tests is equal or more than one, the algorithm will proceed to process 18 and wait for time-date and measuring value data received from the sensing instrument.

After time-date and measuring data have been received, the algorithm will proceed to process 19 and wait for instrument error data received from the sensing meter. Thereafter, the algorithm will check 20 if any errors have been detected. If the time-date data exceeds the one-chip microcomputer 1 batch specific pre-stored expire time-date data, then, the algorithm will return to execute process 16 and the sensing instrument will inform the end-user that zero tests remain and that the expiration date has been exceeded. If the instrument error data received confirm instrument errors 20, then, the algorithm will return to execute process 16 and the sensing instrument will inform the end-user about tests remaining and that an instrument error has occurred.

If during process 20 no error has been detected, the algorithm will proceed to calculate 21 the analyte concentration (y) using the formula y=kx+m, where x is the received measuring data obtained from the sense mean in the sensing instrument, and k is a one-chip microcomputer 1 batch specific pre-stored slope constant, and m is a one-chip microcomputer 1 batch specific pre-stored intercept constant. Process 21 will also reduce the number of remaining tests by one. The algorithm has upon first time execution 50 as the initial number of remaining tests. Thereafter, the algorithm will proceed to process 22 and send the calculated analyte concentration data back to the sensing instrument.

After process 22 the algorithm will return to process 16 which will enable the sensing instrument to display the analyte concentration data and the number of remaining tests to the end-user. The algorithm will then be available to process the next measurement.

It should be understood that the foregoing description is only illustrative of the disclosed subject matter. Different variations, alternatives and modifications can be developed by those skilled in the art without departing from the disclosed subject matter.

While the disclosed subject matter has been described as able to calculate the concentration of a general analyte, some embodiments of the disclosed subject matter can employ chemistries to make other analyte determinations. Such chemistries includes measuring any, for example, of the analytes glucose, albumin, hemoglobin (Hb and HbA1C), myoglobin, troponin (I and T), CK-MB, creatinine kinase (CK), d-dimer, very low density lipoprotein (VLDL), β-type natriuretic peptide (BNP and pro BNP), n-terminal prohormone peptide (NT-proBNP), C-reactive protein (hsCRP and CRP), cystatin C, prothrombin, activated partial thromboplastin (APTT), HCG, LH, FSH, PSA, TSH, T3, T4, AFP, CEA, low density lipoprotein (LDL), high density lipoprotein (HDL), triglycerides, cholesterol, antibodies, *Streptococcus A, Helicobacter Pylori, Salmonella, Chlamydia, Giardia*, cholera, hepatitis (A, B and C), adenovirus, rotavirus, and the like.

While the disclosed subject matter has been described as using an algorithm that calculates the analyte concentration (y) using the formula y=kx+m, where x is the received measuring data obtained from the sense mean in the sensing instrument, and k is a stored batch specific slope constant, and m is a stored batch specific intercept constant value, some embodiments of the invention can use other mathematical formulas including:

$$y=k_1 x^2 + k_2 x + m_1,$$

$$y=k_1 x^3 + k_2 x^2 + k_1 x + m_1,$$

$$y=k_1 \ln x + m_1$$

$$y=k_1 e^x + m_1$$

$$y=k_1 \log x + m_1$$

$$y=k_1 10^x + m_1$$

$$y=k_1 \sin x + m_1$$

$$y=k_1 \cos x + m_1$$

$$y=k_1 \tan x + m_1$$

where $k_{1-2}$ and $m_1$ represent stored batch specific parameter values. It is also possible to replace the formula with reference tables which are used to convert received measuring data obtained from the sense mean in the sensing instrument into an analyte concentration. Alternatively, reference tables can be used in combination with a formula.

While the disclosed subject matter has been described as using a separate data-sending optical transmitter exemplified by a standard light-emitting diode, and a data-receiving optical device exemplified by a standard photo transistor, some embodiments of the disclosed subject matter can use a single standard light-emitting diode (visual light, UV or IR) for bidirectional data transfer as it is know that standard light-emitting diodes are light sensitive devices which can convert light data pulses to voltage/current data pulses.

Furthermore, while the invention has been described as including a one-chip microcomputer such as the PIC10F202, in some embodiments of the invention it is possible to replace the one-chip microcomputer with any one-chip microcomputer including, for example, PIC10F200, PIC10F204, PIC10F206, PIC12C671, PIC12E674, PIC12C508, PIC12C509, PIC12C671, PIC12F629, PIC12F675, PIC12C505, PIC12C54, PIC12C56, PIC16F628, PIC16F676, PIC16F870, M68HC05, M68HC11, M68HC908, P80C31, P80C32, P87C51, P87C52, AT89S51, AT89C51, DS80C320, ST6200, ST6208, ST6215, ST6225, ST7FLITE09, ATtiny15, ATtiny26, ATtiny 2313, SX20AC/DP, SX28AC/SS, MSP430F1121, Z86E0812SSC, or the like.

While the disclosed subject matter has been described as including a one-chip microcomputer which therefore contains a microprocessor, in some embodiments of the disclosed subject matter. the one-chip microcomputer can be replaced with a programmable logic chip exemplified by, for example, MAX II CPLD, Cyclone FPGA, Cyclone II FPGA and the like, or with a microprocessor chip (exemplified by, for example, NTE6809, NTE8080A, MC68882FN16A, Z84C0010PSC, and the like) equipped with an internal memory or external memory chip, or a microprocessor chip equipped with an internal or external oscillator.

While the disclosed subject matter has been described as including a one-chip microcomputer with program execution clocked by an internal oscillator, some embodiments of the disclosed subject matter can provide a clock pulse from an oscillator in the sensing meter without losing execution control of the self-executed algorithm.

While the disclosed subject matter has been described to be powered by an electrical connection from the sensing meter, some embodiments of the disclosed subject matter can be powered with, for example, a battery, an inductive element, a light-to-electricity converting element, or the like.

While the disclosed subject matter has been described as including only a single-chip component, such as a one-chip microcomputer, some embodiments of the disclosed subject matter can further include a plurality of one-chip microcomputers, or, for example, a battery-powered electronic date chip containing a real-time clock, a calendar, or the like, which provides internal time and date information to the said self-executable algorithm.

Accordingly, the present disclosed subject matter is intended to embrace all such alternatives, modifications and variances which fall within the scope of the appended claims.

Having described the disclosed subject matter in detail, it will be apparent that modifications, variations, and equivalent embodiments are possible without departing the scope of the disclosed subject matter defined in the appended claims. Furthermore, it should be appreciated that all examples in the present disclosure are provided as non-limiting examples.

What is claimed is:

1. A disposable analytical microprocessor device for use with a sensing meter and a batch of disposable consumables
    wherein said disposable analytical microprocessor device comprises a microprocessor and memory, said memory comprising at least one stored batch-specific disposable consumable parameter value and at least one self-executable algorithm,
    wherein said analytical microprocessor device is capable of reversible engagement and bi-directional data transfer with said sensing meter,
    wherein said analytical microprocessor device is configured for calculating an analyte concentration value using data received from the sensing meter in combination with mathematical approximation formulas comprised in said stored batch-specific disposable consumable parameter value, and transferring the analyte concentration value to said sensing meter.

2. The device of claim 1 wherein said device comprises a one-chip microcomputer which comprises said microprocessor.

3. The device of claim 1 wherein said reversible engagement enables serial or parallel bidirectional data transfer, or a combination thereof.

4. The device of claim 1 wherein said reversible engagement provides electrical connectivity and further provides said microprocessor with a clock pulse from an oscillator in said sensing meter.

5. The device of claim 1 wherein said reversible engagement is optical and enables serial or parallel bidirectional data transfer, or a combination thereof.

6. The device of claim 1 wherein said self-executable algorithm is based on a reference table conversion, or on a mathematical function approximation wherein said mathematical function is selected from the group comprised of: a linear function, a polynomial function, a logarithmic function, an exponential function, and a trigonometric function.

7. The device of claim 1 wherein said memory is comprised within a one-chip microcomputer comprised in said disposable analytical microprocessor device or within a separate RAM, ROM, EPROM, or EEPROM-based memory chip comprised in said disposable analytical microprocessor device.

8. The device of claim 1 wherein said stored batch-specific disposable consumable parameter values are comprised of information relating to at least one parameter chosen from the group comprised of: specific analyte calculation performance of said batch of disposable consumables, mathematical approximation formulas, encryption keys, analyte name in ASCI-code, a production batch number, a batch production date, a batch expiration date, a number of measurements allowed, analyte identification data, dates of using said disposable consumables, a remaining number of disposable consumables in the batch, an individual identification number of said sensing meter, an individual identification of a person operating said sensing meter, measuring or timing protocols, and high-low alarm level analyte concentration values.

9. The device of claim 8 wherein said stored batch-specific disposable consumable parameter values further include an encrypted key for secure data transfer between said microprocessor and said sensing meter.

10. The device of claim 1 wherein said device further includes a battery powered electronic date chip containing a real-time clock and a calendar which provides internal time and date information to said self-executable algorithm.

11. The device of claim 9,
    wherein said self-executable algorithm is configured to detect a condition selected from the following group: said stored batch-specific disposable consumer parameter values or said data show that a predetermined number of used disposable consumables has been exceeded; the batch expiration has been exceeded; the individual identification number of said sensing meter has been changed; the encrypted key does not corresponds to an encrypted key in said sensing meter; and a measuring procedure error has been reported from said sensing meter, and wherein said self-executable algorithm is configured to disable execution by changing from an active operating state to a non-active operation state upon detection of said condition.

12. A system for use with a disposable consumable for quantitative and qualitative determination of analytes in a biological sample, wherein the system is comprised of the device of claim 1 and a sensing meter.

13. The system of claim 12 wherein said sensing meter further includes means for measuring magnetic permeability changes in said disposable consumable and wherein said sensing meter is operatively coupled to said microprocessor to provide for measurements indicative of manifestations of a chemical or physical reaction in said disposable consumable.

14. The system of claim 12 wherein the said sensing meter further includes means for measuring optical changes in said disposable consumable, and wherein said sensing meter is operatively coupled to said microprocessor to provide for measurements indicative of manifestations of a chemical or physical reaction in said disposable consumable.

15. The system of claim 12 wherein said sensing meter further includes means for measuring electrochemical changes in said disposable consumable, and wherein said sensing meter is operatively coupled to said microprocessor to provide for measurements indicative of manifestations of a chemical or physical reaction in said disposable consumable.

16. The system of claim 12 wherein said sensing meter further includes means for measuring mass changes in said disposable consumable, and wherein said sensing meter is operatively coupled to said microprocessor to provide for measurements indicative of manifestations of a chemical or physical reaction in said disposable consumable.

17. The system of claim 12 wherein said sensing meter further includes sense means for measuring piezoelectric changes or surface plasmon effects in said disposable consumable, and wherein said sensing meter is operatively coupled to said microprocessor to provide for measurements indicative of manifestations of a chemical or physical reaction in said disposable consumable.

18. The system of claim 12 wherein said sensing meter is configured for measuring any of the analytes glucose, albumin, hemoglobin (Hb and HbAl C), myoglobin, troponin (I and T), CK-MB, creatinine kinase (CK), d-dimer, P-type natriuretic peptide (BNP and pro BNP), n-terminal prohormone peptide (NT-proBNP), C-reactive protein (hsCRP and CRP), cystatin C, prothrombin, activated partial thromboplastin (APTT), HCG, LH, FSH, PSA, TSH, T3, T4, AFP, CEA, low density lipoprotein (LDL), High density lipoprotein (HDL), triglycerides, cholesterol, antibodies, *Streptococcus A, Helicobacter Pylori, Salmonella, Chlamydia, Giardia,* cholera, hepatitis (A, B and C), adenovirus, rotavirus or any combination thereof with said disposable consumable, and wherein said sensing meter is operatively coupled to said disposable analytical microprocessor device to provide for measurements indicative of manifestations of a chemical or physical reaction in said disposable consumable.

19. The system of claim 12 wherein the said sensing meter further includes an electronic date chip containing a real-time clock and a calendar which provides time and date information to said self-executable algorithm.

20. A method for determining an analyte concentration in a biological sample, such method comprising; a) applying a biological sample to a disposable analytical microprocessor device of claim 1; and b) introducing said disposable analytical microprocessor device to the sensing meter of claim 12.

* * * * *

UNITED STATES PATENT AND TRADEMARK OFFICE
CERTIFICATE OF CORRECTION

PATENT NO.         : 10,132,820 B2
APPLICATION NO.    : 12/201898
DATED              : November 20, 2018
INVENTOR(S)        : Dario Kriz and Kirstin Ann Kriz It is certified that error appears in the above-identified patent and that said Letters Patent is hereby corrected as shown below:

In the Claims

In Claim 11, Column 10, Line 65, the text reading: "the batch expiration has been exceeded;" should be replaced with --the batch expiration date has been exceeded;--

Signed and Sealed this
Twenty-second Day of January, 2019

Andrei Iancu
*Director of the United States Patent and Trademark Office*